(12) United States Patent
Majeed et al.

(10) Patent No.: US 10,609,935 B2
(45) Date of Patent: Apr. 7, 2020

(54) BEVERAGE COMPOSITIONS CONTAINING BACILLUS COAGULANS MTCC 5856

(71) Applicant: SAMI LABS LIMITED, Bangalore (IN)

(72) Inventors: Muhammed Majeed, Edison, NJ (US); Kalyanam Nagabhushanam, East Windsor, NJ (US); Sivakumar Arumugam, Bangalore (IN); Furqan Ali, Bangalore (IN); Shaheen Majeed, Springville, UT (US)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 15/806,485

(22) Filed: Nov. 8, 2017

(65) Prior Publication Data

US 2018/0338508 A1    Nov. 29, 2018

Related U.S. Application Data

(60) Provisional application No. 62/511,412, filed on May 26, 2017.

(51) Int. Cl.
| | |
|---|---|
| *A61K 35/742* | (2015.01) |
| *A23F 3/30* | (2006.01) |
| *A23L 2/52* | (2006.01) |
| *A23F 5/36* | (2006.01) |

(52) U.S. Cl.
CPC .............. *A23F 5/36* (2013.01); *A23F 3/30* (2013.01); *A23L 2/52* (2013.01); *A61K 35/742* (2013.01); *A23V 2002/00* (2013.01)

(58) Field of Classification Search
None
See application file for complete search history.

(56) References Cited

U.S. PATENT DOCUMENTS 9,579,352 B2 * 2/2017 Majeed ................ A61K 35/742
2015/0313951 A1 * 11/2015 Cash ..................... A23L 33/135
424/93.46

OTHER PUBLICATIONS

Majeed et al International Journal of Food Science and Technology 2016, 51, 894-901 (Year: 2016).*
Hong et al 2005, FEMS Microbiology Reviews 29 ,813-835 (Year: 2005).*
Majeed, M. & Kamarei, 2012, NutraCos, 19-21 (Year: 2012).*
Jurenka 2012 Altern Med Rev, 1:76-81 (Year: 2012).*

* cited by examiner

*Primary Examiner* — Padmavathi Baskar
(74) *Attorney, Agent, or Firm* — Oliff PLC

(57) ABSTRACT

The present invention discloses beverage compositions comprising probiotic *Bacillus coagulans* and water soluble prebiotic fibers that have been subjected to treatments under extreme stress, temperature and pressure conditions like brewing or aeration wherein the spore viability is maintained post said treatments.

6 Claims, No Drawings

… (1)

BEVERAGE COMPOSITIONS CONTAINING BACILLUS COAGULANS MTCC 5856

CROSS-REFERENCE TO RELATED PATENT APPLICATION

This is a non-provisional patent application claiming priority from U.S. Provisional Patent Application No. 62/511,412 filed on 26 May 2017.

BACKGROUND OF THE INVENTION

Field of the Invention

The present invention in general relates to probiotics. More specifically, the present invention relates to beverage compositions comprising probiotic *Bacillus coagulans* strain MTCC 5856.

Description of Prior Art

Probiotics are gaining importance as a dietary supplement owing to their ability to modify the gut microflora yielding increased health benefits. These probiotics can survive the acidic environments of the stomach and small intestine, but are not observed to colonize the gastro-intestinal tract. Thus, there exists a need for constantly supplementing probiotics for the therapeutic benefits to persist.

Beverages are widely consumed food constituents and can be looked upon as a source for co-administering probiotics. It must be noted that beverage compositions are subjected to treatments under extreme stress, temperature and pressure conditions like brewing or aeration wherein the viability of the probiotic spores should be maintained post treatment to result in a successful administration.

United States Patent Application 20090232941 discloses a beverage composition comprising *Bacillus coagulans* strains GBI-30, GBI-20 and GBI-40. United States Patent Application 20130295226 discloses a fruit beverage composition comprising *Lactobacillus paracasei*. Both these applications do not disclose the method of brewing and the survival of the probiotic bacteria in harsh conditions. Also, it is well known in the scientific art that that biological effects of probiotics or products thereof are strain specific and cannot be generalised among genera, species and strains (Probiotics: In Depth/NCCIH, U.S. Department of Health and Human Services, National Institutes of Health). Hence, there still exists a need to find a probiotic strain that is more efficient and viable when subjected to extreme stress, temperature and pressure conditions.

The present invention solves the above technical problem by disclosing a probiotic strain that is viable and efficient when co-administered with beverages.

The principle objective of the inventions is to disclose beverage compositions comprising *Bacillus coagulans* MTCC 5856 wherein the spore viability is maintained post treatments.

The present invention fulfils aforesaid objectives and provides further related advantages.

SUMMARY OF THE INVENTION

The present invention discloses beverage compositions that have been subjected to treatments under extreme stress, temperature and pressure conditions like brewing or aeration and comprise *Bacillus coagulans* MTCC 5856 spores and water soluble prebiotic fibers wherein the spore viability is maintained post said treatments.

DESCRIPTION OF THE MOST PREFERRED EMBODIMENTS

In a principle embodiment, the present invention discloses a beverage composition comprising *Bacillus coagulans* MTCC 5856 in the form of spore and bacterium wherein said bacterial spore has the ability to survive extreme stress, temperature and aeration treatments of said beverage composition. In a related embodiment, the beverage is selected from the group consisting of coffee, tea, fruit juice, aerated soda, malt, energy drinks, chocolate, cocoa, fruit drinks, smoothies, milk shakes, mineral water, cola, cheese spread, honey, tomato ketchup, jam, mayonnaise, protein drink and ice cream. In another related embodiment, the spores include viable or heat killed or dead spores of *Bacillus coagulans* MTCC 5856. In yet another related embodiment, the bacterium includes viable or heat killed or dead or lysed vegetative cells of *Bacillus coagulans* MTCC 5856.

In another preferred embodiment, the invention discloses a coffee composition comprising *Bacillus coagulans* MTCC 5856 in the form of spore and bacterium wherein said bacterial spore is heat resistant having more than 95% viability after brewing coffee. In a related embodiment, the coffee is selected from the group consisting of decaffeinated coffee, unroasted green coffee and roasted coffee. In another related embodiment, the spores include viable or heat killed or dead spores of *Bacillus coagulans* MTCC 5856. In yet another related embodiment, the bacterium includes viable or heat killed or dead or lysed vegetative cells of *Bacillus coagulans* MTCC 5856.

In another related embodiment, the invention discloses a tea composition comprising *Bacillus coagulans* MTCC 5856 in the form of spore and bacterium wherein the said bacterial spore is heat resistant having more than 95% viability after brewing tea. In a related embodiment, the tea includes green tea, black tea, oolong tea, yellow tea, White tea or decaffeinated tea, herbal tea selected from the group consisting of rosehip tea, chamomile tea, jiaogulan tea, peppermint tea, rooibos tea, ginger tea, ginseng tea, or lemon grass tea. In another related embodiment, the spores include viable or heat killed or dead spores of *Bacillus coagulans* MTCC 5856. In yet another related embodiment, the bacterium includes viable or heat killed or dead or lysed vegetative cells of *Bacillus coagulans* MTCC 5856.

In another embodiment, the fruit component of the fruit juice is selected from the group consisting of orange, apple, pears, strawberry, raspberry, cranberry, blue berry, apricot, pineapple, peach, banana, mango, lime, grape, tomato, pomegranate, papaya, tender coconut water, kiwi and a fruit mixture.

In another preferred embodiment, the invention discloses an aerated soda composition comprising *Bacillus coagulans* MTCC 5856 in the form of spore and bacterium wherein the said bacterial spore has the ability to survive aeration. In another related embodiment, the spores include viable or heat killed or dead spores of *Bacillus coagulans* MTCC 5856. In yet another related embodiment, the bacterium includes viable or heat killed or dead or lysed vegetative cells of *Bacillus coagulans* MTCC 5856.

In another preferred embodiment, the present invention discloses a synergistic beverage composition comprising a water soluble prebiotic fiber and *Bacillus coagulans* in the form of spore and bacterium wherein the said bacterial spore has the ability to survive extreme stress, temperature and aeration treatments of said beverage composition. In a related embodiment, the beverage is selected from the group consisting of coffee, tea, fruit juice, aerated soda, malt, energy drinks, chocolate, cocoa, fruit drinks, smoothies, milk shakes, mineral water, cola, cheese spread, honey, tomato ketchup, jam, mayonnaise, protein drink and ice cream. In another related embodiment the water soluble prebiotic fiber is selected from the group consisting of fructooligosaccharides (FOS), Galacto-oligosaccharide (GOS), Inulin and polydextrose. In another related embodiment, the spores include viable or heat killed or dead spores of *Bacillus coagulans*. In yet another related embodiment, the bacterium includes viable or heat killed or dead or lysed vegetative cells of *Bacillus coagulans*.

In another preferred embodiment, the invention discloses a synergistic coffee composition comprising a prebiotic water soluble fiber and *Bacillus coagulans* in the form of spore and bacterium wherein the said bacterial spore is heat resistant having more than 95% viability after brewing coffee. In a related embodiment, coffee includes decaffeinated coffee, unroasted green coffee and roasted coffee. In another related embodiment the water soluble prebiotic fiber is selected from the group consisting of fructooligosaccharides (FOS), Galacto-oligosaccharide (GOS), Inulin and polydextrose. In another related embodiment, the spores include viable or heat killed or dead spores of *Bacillus coagulans*. In yet another related embodiment, the bacterium includes viable or heat killed or dead or lysed vegetative cells of *Bacillus coagulans*. In a preferable related embodiment, the *Bacillus coagulans* strain is preferably *Bacillus coagulans* MTCC 5856 and also the strains derived from *Bacillus coagulans* Hammer strain accession number ATCC 31284 and ATCC 7050

In another related embodiment, the invention discloses a synergistic tea composition comprising a prebiotic water soluble fiber and *Bacillus coagulans* in the form of spore and bacterium wherein the said bacterial spore is heat resistant having more than 95% viability after brewing tea. In a related embodiment, the tea includes green tea, black tea, oolong tea, yellow tea, white tea or decaffeinated tea, herbal tea selected from the group consisting of rosehip tea, chamomile tea, jiaogulan tea, peppermint tea, rooibos tea, ginger tea, ginseng tea, or lemon grass tea. In another related embodiment the water soluble probiotic fiber is selected from the group consisting of fructooligosaccharides (FOS), Galacto-oligosaccharide (GOS), Inulin and polydextrose. In another related embodiment, the spores include viable or heat killed or dead spores of *Bacillus coagulans*. In yet another related embodiment, the bacterium includes viable or heat killed or dead or lysed vegetative cells of *Bacillus coagulans*. In a preferable related embodiment, the *Bacillus coagulans* strain is preferably *Bacillus coagulans* MTCC 5856, and also the strains derived from *Bacillus coagulans* Hammer strain accession number ATCC 31284 and ATCC 7050

The aforesaid most preferred embodiments incorporating the technical features and technical effects of instant invention, are explained through illustrative examples herein under.

Example 1: Methods Employed for Brewing Coffee and Tea with *Bacillus coagulans* MTCC 5856

*Bacillus coagulans* MTCC 5856 Stability During Coffee Brewing

Commercial preparation of *Bacillus coagulans* MTCC 5856 spores was standardized to $15 \times 10^9$ cfu (spores) per gram and added to grounded unroasted green coffee or roasted coffee and blended at room temperature with low r.p.m. for 60 min. Further, 1.0 g of water soluble prebiotic fibres (fructooligosaccharide, galacto-oligosaccharides, inulin and polydextrose) were added to 4.0 gm of unroasted green coffee or roasted coffee and blended at room temperature with low r.p.m. for 60 min (Table 1). Approximately 5.0 g of the compositions were brewed using electric brewer and tested for viable spore count as per method described earlier (Majeed et al., World J Microbiol Biotechnol (2016) 32; 60). Average mean of spore viable counts are expressed in $\log_{10}$ CFU.

TABLE 1

Formulation of Coffee beverages

| Formulation | *Bacillus coagulans* MTCC 5856 ($15 \times 10^9$ spores/gm) | #Coffee and beverage excipient + Prebiotic Fibre* (grams) | Total weight per serving |
|---|---|---|---|
| 01 | 0.144 g | 3.96 + 0.04 + 0.0 | 5.144 |
| 02 | 0.072 g | 3.96 + 0.04 + 1.0 | 5.072 |
| 03 | 0.144 g | 3.96 + 0.04 + 1.0 | 5.144 |
| 04 | 0.288 g | 3.96 + 0.04 + 1.0 | 5.288 | where coffee is unroasted green coffee beans and Roasted coffee beans.
*Where the prebiotic fibres are FOS, GOS, Inulin and polydextrose

*Bacillus coagulans* MTCC 5856 Stability During Tea (Black, Green and Oolong Tea) Brewing Commercial preparation of *Bacillus coagulans* MTCC 5856 was standardized to $15 \times 10^9$ cfu (spores) per gram and added to black, green or oolong tea and blended at room temperature with low r.p.m. for 60 min. Further, 1.0 g of water soluble prebiotic fibres (fructooligosaccharide, galacto-oligosacharides, inulin and polydextrose) were added to 4.0 gm of black, green or oolong tea and blended at room temperature with low r.p.m. for 60 min (Table 2). Approximately 5.0 g of these tea compositions were brewed using electric brewer and tested for viable spore count as per method described earlier (Majeed et al., World J Microbiol Biotechnol (2016) 32:60). Average mean of spore viable counts are expressed in log 10 CFU.

TABLE 2

Formulation of tea beverages

| Formulation | *Bacillus coagulans* MTCC 5856 ($15 \times 10^9$ spores/gm) | #Tea and beverage excipient + Prebiotic Fibre* (grams) | Total weight per serving |
|---|---|---|---|
| 01 | 0.15 g | 3.96 + 0.04 + 0.0 | 4.15 |
| 02 | 0.075 g | 3.96 + 0.04 + 1.0 | 5.075 |
| 03 | 0.15 g | 3.96 + 0.04 + 1.0 | 5.15 |
| 04 | 0.30 g | 3.96 + 0.04 + 1.0 | 5.30 |

Where the tea are black, green and oolong.
*Where the prebiotic fibres are FOS., GOS, Inulin and polydextrose Effect of Gastric Stress and Brewing Conditions on the Germination of *Bacillus coagulans* MTCC 5856 Spores The effect of gastric stress on the *Bacillus coagulans* MTCC 5856 spores was studied by treating brewed coffee or tea (as described in above paragraph) in acidic conditions. The pH of brewed coffee or tea was adjusted aseptically to 1.5 using 2 N HCl and incubated at 37° C. for 3 h with low r.p.m. After 3 h of incubation, again pH was adjusted aseptically back to 7.0 using 2 N NaOH and 0.5% (w/v) ox bile was added to tea or coffee flask. Oxygen reducing enzyme Oxyrase (Oxyrase® for Broth, Oxyrase, Inc. Mansfield, Ohio, USA) was also added to each flask. Further flasks were incubated at 37° C. for 24 h with low r.p.m. pH values at 0 h of incubation and after 24 h of incubation were also recorded. Optical density (OD) at 600 nm was recorded at 0 h and after 24 of incubation by diluting the sample into sterilized demineralized water to 1:5.

Example 2: Results for Brewing Coffee and Tea with *Bacillus coagulans* MTCC 5856 Brewed Coffee with *Bacillus coagulans* MTCC 5856

The thermo-stability and compatibility of *Bacillus coagulans* MTCC 5856 spores in coffee was evaluated during brewing using electric brewer. Stainless steel and paper filter were used in brewer to understand the feasibility of probiotic brewing. There was 0.5 $Log_{10}$ cfu (spores) reduction after brewing which remained almost same even after 10 min of incubation at room temperature (Table 3). The data suggested that *Bacillus coagulans* MTCC 5856 spores remained 94.83% viable after brewing using Stainless steel filter. There was no significant difference observed when coffee was brewed using stainless steel or paper filters.

TABLE 3

Viability of *B. coagulans* MTCC 5856 during Coffee brewing using electric brewer

| Time | Brewed and filtered using SS filter | | Brewed and filtered using paper filter | |
|---|---|---|---|---|
| | $Log_{10}$ CFU/10 g | Viability (%) | $Log_{10}$ CFU/10 g | Viability (%) |
| Post Brew | 9.8388 ± 0.012 | 100 | 9.8388 ± 0.012 | 100 |
| After Brew | 9.3304 ± 0.011 | 94.83 | 9.2600 ± 0.014 | 94.11 |
| After 10 min | 9.3096 ± 0.013 | 94.63 | 9.2504 ± 0.012 | 94.01 |

Brewed Tea with *Bacillus coagulans* MTCC 5856

Black tea, green tea and oolong tea were supplemented with *Bacillus coagulans* MTCC 5856 spores and brewed to determine the spore survival during brewing. *Bacillus coagulans* MTCC 5856 spores were found to be highly stable and the viability remained above 99% after brewing (Table 4 & 5).

Same brewed tea samples were chilled for 72 h and then spore viability was determined. The viability of spores in black, green and oolong tea after chilling for 72 h was 95.13%, 93.58% and 94.51% respectively (Table 4 & 5).

TABLE 5

Viability of *B. coagulans* MTCC 5856 during green and oolong tea brewing using electric brewer

| | Green Tea | | Oolong Tea | |
|---|---|---|---|---|
| Time | $Log_{10}$ CFU/serving | Viability (%) | $Log_{10}$ CFU/serving | Viability (%) |
| Post Brew | 9.4471 ± 0.011 | 100 | 9.4313 ± 0.012 | 100 |
| After Brew | 9.3830 ± 0.012 | 99.32 | 9.3921 ± 0.011 | 99.58 |
| After 10 min | 9.371 ± 0.013 | 99.19 | 9.3842 ± 0.014 | 99.50 |
| After 72 h chilling | 8.841 ± 0.014 | 93.58 | 8.914 ± 0.012 | 94.51 |

Germination of Spores

To deliver the right amount of viable *Bacillus coagulans* MTCC 5856 spores in the human gut, the effect of brewing conditions and gastric stress on the germination of *Bacillus coagulans* MTCC 5856 spores was conducted. Tea and coffee along with the *Bacillus coagulans* MTCC 5856 spores were brewed and then subjected to gastric stress (acid and bile) followed by anaerobic incubation at 37° C. with bile salts to mimic human conditions. This set of experiment was conducted to understand the spore germination when *Bacillus coagulans* MTCC 5856 is brewed and digested by human. Additionally, along with tea and coffee *B. coagulans* MTCC 5856 was brewed with water soluble prebiotic fibres (fructooligosaccharide, galacto-oligosacharides, inulin and polydextrose). Results of the experiment revealed that *B. coagulans* MTCC 5856 spores could germinate after brewing and surviving in harsh condition of gastric stress by using tea or coffee as sole nutritional source (Table 6). Additionally, there was further increase in the germination by the addition of water soluble prebiotic fibres (Table 6). This suggested that soluble prebiotic fibres have synergistic effect along with tea and coffee on the germination of *B. coagulans* MTCC 5856 spores.

TABLE 4

Viability of *B. coagulans* MTCC 5856 during black tea brewing using electric brewer

| | Formulation-01 | | Formulation-02 | | Formulation-03 | |
|---|---|---|---|---|---|---|
| Time | $Log_{10}$ serving | CFU/Viability (%) | $Log_{10}$ serving | CFU/Viability (%) | $Log_{10}$ serving | CFU/Viability (%) |
| Initial count | 8.9309 ± 0.011 | 100.00 | 9.1182 ± 0.012 | 100.00 | 9.4667 ± 0.010 | 100.00 |
| Post Brew | 9.1760 ± 0.014 | 102.74 | 9.1846 ± 0.011 | 100.73 | 9.6570 ± 0.014 | 102.01 |
| After 10 min | 9.1583 ± 0.011 | 102.55 | 9.1760 ± 0.010 | 100.63 | 9.6683 ± 0.011 | 102.13 |
| After 72 h chilling | 8.6570 ± 0.012 | 96.93 | 8.6739 ± 0.012 | 95.13 | 9.2878 ± 0.011 | 98.11 |

TABLE 6

Germination of *Bacillus coagulans* MTCC 5856 in gastric stress using tea and coffee or in combination with water soluble prebiotic fibres as nutritional source

| S. No. | Probiotic Composition | OD at 600 nm (1:5 dilution) 0 h | OD at 600 nm (1:5 dilution) 24 h | % Increase in growth |
|---|---|---|---|---|
| 1 | Black Tea + *B. coagulans* MTCC 5856 | 0.083 ± 0.001 | 0.156 ± 0.01 | 46.79 |
| 2 | Black Tea + FOS + *B. coagulans* MTCC 5856 | 0.091 ± 0.002 | 0.185 ± 0.01 | 50.81 |
| 3 | Black Tea + GOS + *B. coagulans* MTCC 5856 | 0.085 ± 0.001 | 0.187 ± 0.02 | 54.54 |
| 4 | Black Tea + Inulin + *B. coagulans.* MTCC 5856 | 0.088 ± 0.001 | 0.191 ± 0.01 | 53.92 |
| 5 | Black Tea + Polydextrose + *B. coagulans* MTCC 5856 | 0.092 ± 0.001 | 0.188 ± 0.02 | 51.06 |
| 6 | Green Tea + *B. coagulans* MTCC 5856 | 0.075 ± 0.001 | 0.112 ± 0.02 | 33.03 |
| 7 | Green Tea + FOS + *B. coagulans* MTCC 5856 | 0.078 ± 0.002 | 0.125 ± 0.01 | 37.60 |
| 8 | Green Tea + GOS + *B. coagulans* MTCC 5856 | 0.075 ± 0.001 | 0.145 ± 0.03 | 48.27 |
| 9 | Green Tea + Inulin + *B. coagulans* MTCC 5856 | 0.079 ± 0.003 | 0.141 ± 0.01 | 43.97 |
| 10 | Green Tea + Polydextrose + *B. coagulans* MTCC 5856 | 0.074 ± 0.002 | 0.142 ± 0.02 | 47.88 |
| 11 | Oolong Tea + *B. coagulans* MTCC 5856 | 0.084 ± 0.001 | 0.123 ± 0.01 | 31.70 |
| 12 | Oolong Tea + FOS + *B. coagulans* MTCC 5856 | 0.082 ± 0.001 | 0.162 ± 0.02 | 49.38 |
| 13 | Oolong Tea + GOS + *B. coagulans* MTCC 5856 | 0.085 ± 0.003 | 0.159 ± 0.01 | 46.54 |
| 14 | Oolong Tea + Inulin + *B. coagulans* MTCC 5856 | 0.086 ± 0.001 | 0.159 ± 0.01 | 45.91 |
| 15 | Oolong Tea + Polydextrose + *B. coagulans* MTCC 5856 | 0.085 ± 0.002 | 0.157 ± 0.01 | 45.85 |
| 16 | Coffee + *B. coagulans* MTCC 5856 | 0.142 ± 0.001 | 0.361 ± 0.01 | 60.66 |
| 17 | Coffee + FOS + *B. coagulans* MTCC 5856 | 0.139 ± 0.001 | 0.521 ± 0.02 | 73.32 |
| 18 | Coffee + GOS + *B. coagulans* MTCC 5856 | 0.154 ± 0.002 | 0.531 ± 0.03 | 70.99 |
| 19 | Coffee + Inulin + *B. coagulans* MTCC 5856 | 0.145 ± 0.001 | 0.516 ± 0.01 | 71.89 |
| 20 | Coffee + Polydextrose + *B. coagulans* MTCC 5856 | 0.144 ± 0.003 | 0.532 ± 0.02 | 72.93 |

Example 3: Beverage Compositions with *Bacillus coagulans* MTCC 5856

The viability of *Bacillus coagulans* MTCC 5856 was also tested in other beverages like aerated soda/cola, fruit juices, mineral water, chocolate, cocoa, fruit drinks, smoothies, milk shakes, cheese spread, honey, tomato ketchup, jam, mayonnaise, protein drink and ice cream. The results are tabulated in tables 7 & 8.

TABLE 7

Stability and recovery of *Bacillus coagulans* Spores in beverages

| Time | Soda drink with *B. coagulans* MTCC 5856 $\text{Log}_{10}$ CFU/serving | Soda drink with *B. coagulans* MTCC 5856 Viability (%) | Timms Up with *B. coagulans* MTCC 5856 $\text{Log}_{10}$ CFU/serving | Timms Up with *B. coagulans* MTCC 5856 Viability (%) | Orange Juice with *B. coagulans* MTCC 5856 $\text{Log}_{10}$ CFU/serving | Orange Juice with *B. coagulans* MTCC 5856 Viability (%) | Sprite with *B. coagulans* MTCC 5856 $\text{Log}_{10}$ CFU/serving | Sprite with *B. coagulans* MTCC 5856 Viability (%) | Mineral Water with *B. coagulans* MTCC 5856 $\text{Log}_{10}$ CFU/serving | Mineral Water with *B. coagulans* MTCC 5856 Viability (%) |
|---|---|---|---|---|---|---|---|---|---|---|
| Expected Recovery | 9.301 | 100 | 9.301 | 100 | 9.301 | 100 | 9.301 | 100 | 9.301 | 100 |
| After 24 h | 8.612 | 92.59 | 8.454 | 92.59 | 9.217 | 99.1 | 8.204 | 88.21 | 9.26 | 99.56 |

TABLE 8

Stability of *B. coogulans* MTCC 5856 spores during the process of preparation of various foods and beverage mix and its recovery

| S. No. | Sample | $\text{Log}_{10}$ CFU/serving | % Recovery |
|---|---|---|---|
| 1 | Dry Fruit (Cashew) with *B. coagulans* MTCC 5856 (20 g serving) | 8.781 | 94.41 |
| 2 | Chocolate with *B. coagulans* MTCC 5856 (50 g serving) | 9.25 | 99.45 |
| 3 | Cheese Spread with *B. coagulans* MTCC 5856 (50 g serving) | 9.26 | 99.56 |
| 4 | Honey with *B. coagulans* MTCC 5856 (50 g serving) | 9.13 | 98.16 |
| 5 | Mixed Fruit Jam with *B. coagulans* MTCC 5856 (50 g serving) | 8.989 | 96.65 |
| 6 | Tomato Ketchup with *B. coagulans* MTCC 5856 (50 g serving) | 9.065 | 97.46 |
| 7 | Mayonnaise with *B. coagulans* MTCC 5856 (50 g serving) | 8.958 | 96.31 |
| 8 | Protein Drink Mix with *B. coagulans* MTCC 5856 (50 g serving) | 9.274 | 99.71 |

TABLE 8-continued

Stability of *B. coogulans* MTCC 5856 spores during the process of preparation of various foods and beverage mix and its recovery

| S. No. | Sample | Log$_{10}$ CFU/serving | % Recovery |
|---|---|---|---|
| 9 | Soy Milk with *B. coagulans* MTCC 5856 (50 g serving) | 8.238 | 88.57 |
| 10 | Shrikhand with *B. coagulans* MTCC 5856 (50 g serving) | 9.064 | 97.45 |
| 11 | Ice-cream with *B. coagulans* MTCC 5856 (30 g serving) | 7.99 | 85.90 |

The results indicated that *B. coagulans* MTCC 5856 is stable in all beverage compositions with increased viability and recovery.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

We claim:

1. A beverage composition comprising *Bacillus coagulans* MTCC 5856 in the form of spore and bacterium wherein the bacterial spore has the ability to survive extreme stress, temperature and aeration treatments of the beverage composition, wherein the beverage composition is tea, wherein the tea is selected from the group consisting of green tea, black tea, oolong tea, yellow tea, white tea, decaffeinated tea, rosehip tea, chamomile tea, jiaogulan tea, peppermint tea, rooibos tea, ginger tea, *ginseng* tea, or lemon grass tea.

2. The composition as in claim 1, wherein the spores comprise viable or heat killed or dead spores of *Bacillus coagulans* MTCC 5856.

3. The composition as in claim 1, wherein the bacterium comprises viable or heat killed or dead or lysed vegetative cells of *Bacillus coagulans* MTCC 5856.

4. The composition as in claim 1, wherein
the bacterial spore is heat resistant having more than 95% viability after brewing the tea.

5. The composition as in claim 4, wherein the spores comprise viable or heat killed or dead spores of *Bacillus coagulans* MTCC 5856.

6. The composition as in claim 4, wherein the bacterium comprises viable or heat killed or dead or lysed vegetative cells of *Bacillus coagulans* MTCC 5856.

* * * * *